United States Patent [19]

Brunner

[11] Patent Number: 4,797,152
[45] Date of Patent: Jan. 10, 1989

[54] CYCLOHEXENONECARBOXYLIC ACID DERIVATIVES WITH HERBICIDAL AND PLANT GROWTH REGULATING PROPERTIES

[75] Inventor: Hans-Georg Brunner, Lausen, Switzerland

[73] Assignee: Ciba-Geigy Corporation, Ardsley, N.Y.

[21] Appl. No.: 930,829

[22] Filed: Nov. 14, 1986

Related U.S. Application Data

[62] Division of Ser. No. 714,133, Mar. 20, 1986, Pat. No. 4,640,706.

[30] Foreign Application Priority Data

Mar. 30, 1984 [CH] Switzerland ............... 1613/84

[51] Int. Cl.$^4$ ............... A01N 37/18; C07C 103/19
[52] U.S. Cl. ............... 71/118; 71/105; 71/98; 71/95; 71/94; 546/226; 548/539; 558/412; 564/191; 564/188; 564/168; 564/167; 564/166; 564/164; 564/163; 564/162
[58] Field of Search ............... 564/191, 162, 166, 164, 564/167, 168, 163, 188; 71/118, 94, 95, 98, 105; 548/539; 546/226; 558/412

[56] References Cited

U.S. PATENT DOCUMENTS

| | | | |
|---|---|---|---|
| 3,950,420 | 4/1976 | Sawaki et al. | 71/88 |
| 3,989,737 | 11/1976 | Sawaki et al. | 71/88 |
| 4,011,256 | 3/1977 | Sawaki et al. | 560/125 |
| 4,440,566 | 4/1984 | Luo | 71/98 |
| 4,584,013 | 7/1986 | Brunner | 71/94 |
| 4,618,360 | 10/1986 | Brunner | 71/88 |
| 4,662,382 | 11/1986 | Brunner | 71/94 |

FOREIGN PATENT DOCUMENTS

2110673 4/1983 United Kingdom .

*Primary Examiner*—Nicky Chan
*Attorney, Agent, or Firm*—Kevin T. Mansfield; Edward McC. Roberts

[57] ABSTRACT

Novel cyclohexenonecarboxylic acid derivatives exhibit herbicidal and plant growth regulating activity.

The cyclohexanedionecarboxylic derivatives are of the formula I

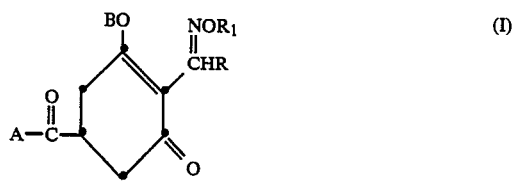

wherein

A is an aliphatic or aromatic alcohol, or is an amino group which may be substituted by halogen, lower alkoxy, lower alkylthio, nitro or cyano, or is a heterocyclic amino group which is unsubstituted or substituted, R is $C_1$–$C_6$alkyl or $C_3$–$C_6$cycloalkyl, each unsubstituted or substituted by halogen, $C_1$–$C_4$alkoxy or $C_1$–$C_4$alkylthio, $R_1$ is $C_1$–$C_6$alkyl, $C_1$–$C_6$haloalkyl, $C_3$–$C_6$alkenyl, $C_3$–$C_6$haloalkenyl or $C_3$–$C_6$alkylnyl, B is an aliphatic or aromatic radical or is an aliphatic or aromatic carbonyl or sulfonyl group which may be substitued by halogen, lower alkoxy, lower alkylthio, nitro or cyano.

The compounds are suitable for selectively controlling grasses in crops of useful plants.

8 Claims, No Drawings

CYCLOHEXENONECARBOXYLIC ACID DERIVATIVES WITH HERBICIDAL AND PLANT GROWTH REGULATING PROPERTIES

This is a divisional of application Ser. No. 714,133 filed on Mar. 20, 1986, now U.S. Pat. No. 4,640,706, issued Feb. 3, 1987.

The present invention relates to novel cyclohexenonecarboxylic acid derivatives with herbicidal and plant growth regulating properties, to compositions containing said cyclohexanedionecarboxylic acid derivatives, as well as to the use of said derivatives for controlling weeds selectively and totally and for regulating plant growth.

The novel cyclohexanedionecarboxylic acid derivatives are of the formula I $$\text{(I)}$$

wherein

A is an $-OR_2$ or $-NR_3R_4$ radical,

R is $C_1-C_6$alkyl or $C_3-C_6$cycloalkyl, each unsubstituted or substituted by halogen, $C_1-C_4$alkoxy or $C_1-C_4$alkylthio, $R_1$ is $C_1-C_6$alkyl, $C_1-C_6$haloalkyl, $C_3-C_6$alkenyl, $C_3-C_6$haloalkenyl or $C_3-C_6$alkynyl, $R_2$ and $R_3$ are each independently of the other hydrogen; $C_1-C_6$alkyl, $C_1-C_6$haloalkyl, $C_2-C_{10}$alkoxyalkyl, $C_2-C_{10}$alkylthioalkyl; or are $C_3-C_6$alkenyl which is unsubstituted or substituted by halogen, $C_1-C_4$alkoxy or $C_1-C_4$alkylthio; or are $C_3-C_6$alkynyl; or are phenyl or $C_1-C_6$aralkyl, the phenyl nucleus of which is unsubstituted or substituted by halogen, $C_1-C_4$alkyl, $C_1-C_4$alkoxy, $C_1-C_4$haloalkyl, nitro or cyano, $R_4$ is $C_1-C_4$alkoxy or has the same meaning as $R_2$, $R_3$ and $R_4$ together with the nitrogen atom to which they are attached are also a 5- or 6-membered heterocycle which may contain an additional oxygen or sulfur atom in the ring, B is a $-COR_5$, $-SO_2R_5$ or $R_6$ radical, $R_5$ is $C_1-C_6$alkyl, $C_3-C_6$alkenyl, $C_3-C_6$alkynyl, or also phenyl or benzyl which is unsubstituted or substituted by halogen, $C_1-C_4$alkyl, $C_1-C_4$haloalkyl, $C_1-C_4$alkoxy, $C_1-C_4$haloalkoxy, nitro or cyano, $R_6$ is $C_1-C_6$alkyl, $C_3-C_6$alkenyl, $C_3-C_6$alkynyl, or also benzyl which is unsubstituted or substituted as above.

In the above definitions, alkyl denotes straight chain and branched alkyl, e.g. methyl, ethyl, propyl, isopropyl, butyl, isobutyl, sec-butyl, tert-butyl, as well as all stereoisomeric forms of the higher homologues. Alkenyl and alkynyl likewise denote straight chain and branched radicals, e.g. vinyl, allyl, methallyl, butenyl, methylbutenyl, dimethylbutenyl, ethynyl, propynyl, butynyl, methylbutynyl, dimethylbutynyl.

Halogen denotes fluorine, chlorine, bromine or iodine atoms.

5- or 6-membered heterocycles $-NR_3R_4$ which may contain an additional oxygen or sulfur atom in the ring will be understood as meaning pyrrole, pyrrolidine, piperidine, morpholine or also thiomorpholine radicals. Such rings may be substituted by methyl groups.

The cyclohexenonecarboxylic acid derivatives of formula I have good herbicidal and plant growth regulating action.

Compounds having particularly good action comprise the following groups:

cyclohexane derivatives of formula Ia;

compounds of formula I, wherein A is an amino group $-NR_3R_4$ and B is an acyl radical $-COR_5$, preferably dimethyl 3-acetoxy-4-(1-ethoximinobutyl)-5-oxocyclohex-3-enecarboxamide and dimethyl 3-benzyloxy-4-(1-ethoximinobutyl)-5-oxocyclohex-3-enecarboxamide;

compounds of formula I, wherein A is an amino group $-NR_3R_4$ and B is an $R_6$ radical, preferably dimethyl 3-methoxy-4-(1-ethoximinobutyl)-5-oxocyclohex-3-enecarboxamide;

compounds of formula I, wherein A is an amino group $-NR_3R_4$ and B is a sulfonyl group $-SO_2R_5$;

compounds of formula I, wherein A is an alkanol radical $-OR_2$ and B is an acyl radical $-COR_5$;

compounds of formula I, wherein A is an alkanol radical $-OR_2$ and B is a sulfonyl group $-SO_2R_5$; and compounds of formula I, wherein A is an alkanol radical $-OR_2$ and B is an $R_6$ radical.

Depending on the reaction conditions and the substsitutents, the oxime compounds are obtained as E and Z isomers.

The novel cyclohexenonecarboxylic acid derivatives of formula I are prepared in a manner known per se by reacting a 3,5-cyclohexanedionecarboxylic acid derivative or a 3-hydroxy-5-oxocyclohexenecarboxylic acid derivative of formula II $$\text{(II)}$$

wherein A, R and $R_1$ are as defined above, with a reactive ester of a compound of formula III $$BZ \quad \text{(III)}$$

wherein B is as defined in claim 1, and Z is a starting group, in an inert organic solvent and in the presence of a base.

The compounds of formula BZ are either alkyl halides, carboxylic acid derivatives or sulfonic acid derivatives. Suitable reactive acid derivatives are in particular the acid halides and also esters and mixed anhydrides with lower fatty acids, e.g. the acetate, and acid anhydrides of the formula BCOOCOB or, if B is an $R_6$ radical, also the methylsulfonic, tolylsulfonic or benzenesulfonic acid radicals thereof.

Suitable inert organic solvents for this reaction are in particular aromatic compounds such as benzene or toluene, hydrogen halides such as chloroform, dichloroethane or carbon tetrachloride, or also ketones and esters such as acetone or ethyl acetate.

The reaction temperatures are in the range from room temperature to the boiling point of the reaction mixture. During the addition of acid chloride it may be necessary to cool the reaction vessel.

Suitable bases are both organic and inorganic bases. Examples of such bases are pyridine, 4-aminopyridine, collidine, triethylamine, amonium carbonate, sodium carbonate, potassium carbonate or calcium carbonate or the corresponding bicarbonates.

The starting cyclohexanedionecarboxylic acid derivatives are obtained from 3,5-dihydroxybenzoic acid. The benzoic acid is first hydrogenated with hydrogen in the presence of Raney nickel, and then esterified or amidated at the acid radical. If necessary, the keto group is protected e.g. as enol ether or enamine [q.v. J. Am. Chem. Soc. 78, 4405 (1956)].

The same 3,5-dioxocyclohexanecarboxylic acid derivative can also be obtained by hydrogenating a 3,5-dihydroxybenzoate or an amide q. v. Arch. Pharm. 307 577 (1974)].

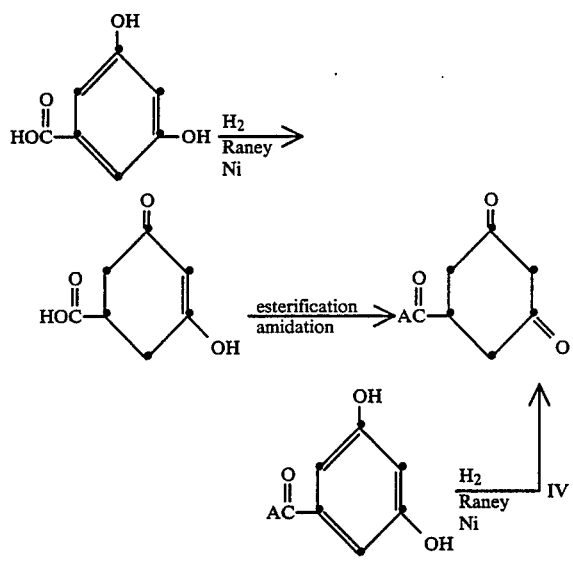

The 3,5-dicyclohexanecarboxylic acid derivative of formula IV so obtained is then reacted in an inert organic solvent and in the presence of a base with an acid halide of formula V HalCOR wherein R is as defined above. The resultant product is then isolated and optionally further reacted in an inert water-immiscible solvent at boiling temperature and under dehydrating conditions with a hydroxylamine of formula VI

HOHNR$_1$ wherein R$_1$ is as defined above, in accordance with the scheme

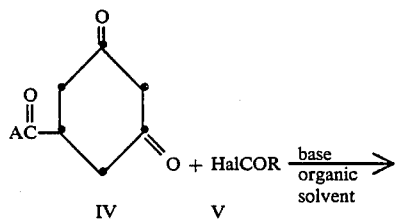

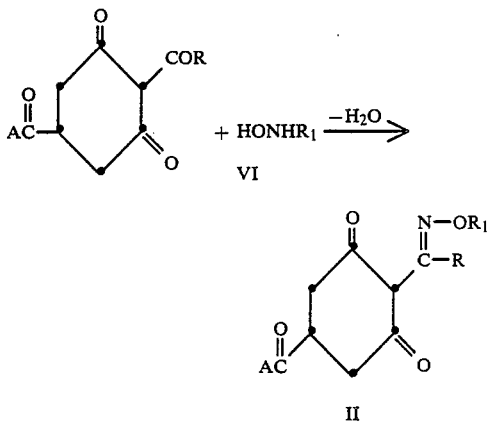

Here, too, suitable solvents for these reactions are aromatic compounds and hydrogen halides. The abovementioned bases can be used.

The reaction temperatures are in the range from room temperature to the boiling temperature of the reaction mixture. During the addition of acid chloride it is necessary to cool the reaction vessel.

Suitable acid halides of formula V are in particular acetyl chloride, propionyl chloride, butyryl chloride, valeryl chloride, 3-methoxypropionyl chloride, 2-chloropropionyl chloride, cyclopropanoyl chloride or cyclohexanoyl chloride, and the corresponding bromides. The preparation of these starting materials is described in Swiss patent application No. 6747/83-0. The preparation of such a compound is described in more detail in Example Ia–Ic herein.

The compounds of formula I exhibit herbicidal and plant growth regulating activity and are suitable e.g. for selectively controlling grasses in crops of useful plants.

When used at low rates of application, the compounds of formula I have good selective growth inhibiting and selective herbicidal properties which make them most suitable for use in crops of useful plants, especially in sugar beet, cereals, cotton, soybeans, maize and rice. In some cases damage is also caused to weeds which have only been controlled up to now with total herbicides.

The compounds of formula I have in addition pronounced plant growth regulating properties which can take the form of an increase in yield of cultivated plants or harvest produce. Moreover, many compounds of formula I have a plant growth inhibiting action which is dependent on the concentrations in which the compounds are applied. The growth of both monocots and dicots is inhibited. Thus, for example, the compounds of formula I selectively inhibit the growth of luguminosae which are frequently planted as cover crops in tropical regions, so that, while soil erosion between cultivated plants is prevented, the cover corps cannot compete with the cultivated plants.

Inhibition of the vegetative growth of many cultivated plants permits more plants to be sown in a crop area, so that a higher yield may be obtained per unit of area.

A further mechanism of yield increase using growth regulators resides in the fact that nutrients are able increasingly to promote flower formation and fruiting, whereas vegetative growth is inhibited.

Inhibition of the vegetative growth of monocots, e.g. grasses or also cultivated plants such as cereals, is sometimes desirable and advantageous. Such a growth inhibition is of economic interest, inter alia, in respect of grasses, as the frequency of cutting in flower gardens, parks, sports fields and road shoulders can thereby be reduced. Of importance too is the inhibition of the growth of herbaceous and ligneous plants on road shoulders and near transmission lines, or generally in areas in which strong growth is undesirable.

The use of growth regulators for inhibiting the growth in height of cereals is also important, as shortening the stalks diminishes or completely eliminates the danger of lodging before harvesting. In addition, growth regulators are able to bring about a strengthening of the stalks in crops of cereals and this too counteracts lodging.

Further, the compounds of formula I are suitable for preventing stored potatoes from seeding. During winter storage, potatoes often develop sprouts which result in shrinkage, weight loss, and rot. At higher rates of application, all tested plants are so severely damaged in their development that they die.

The invention also relates to herbicidal and plant growth regulating compositions which contain a novel compound of formula I, and also to methods of controlling weeds pre- and postemergence and of inhibiting the growth on monocots and dicots, especially grasses, tropical cover crops and tobacco plant suckers.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of applications, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates. The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981; M. and J. Ash, "Encyclopedia of Surfactants", Vol. I-III, Chemical Publishing Co., New York, 1980-81.

The active ingredient formulations usually contain 0.1 to 95%, preferably 0.1 to 80%, of a compound of formula I, 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% of active ingredient. The rates of application are normally from 0.001 to 10 kg a.i./ha, preferably from 0.025 to 5 kg a.i./ha.

The compositions may also contain further ingredients such as stabilisers, antifoams, viscosity regulators, binders, tackifiers, as well as fertilisers and other compounds for obtaining special effects.

PREPARATORY EXAMPLES

EXAMPLE 1

Preparation of dimethyl 4-(1-ethoxyaminobutylidene)-3,5-cycLohexanedionecarboxamide (intermediate)

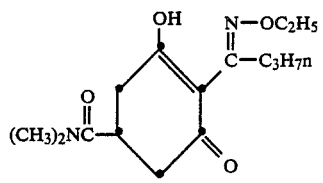

(a) With stirring, 18.4 ml of dimethylcarbamoyl chloride are added dropwise to a solution of 15.6 g of cyclohexanedionecarboxylic acid in 50 ml of pyridine and the reaction mixture is then stirred further for 12 hours at room temperature and then for 2 hours at boiling temperature under reflux. After cooling, the reaction mixture is taken up in 400 ml of ethyl acetate, the organic phase is washed with four portions of brine, dried over magnesium sulfate and concentrated. The residue consists of crude dimethyl 3-(N,N-dimethylcarbamoyl)-5-oxocyclohex-(3)-enecarboxamide. This is dissolved in 300 ml of tetrahydrofuran, then 8 ml of concentrated hydrochloric acid are added and the reaction mixture is stirred for 2 hours at room temperature. The reaction mixture is then washed with brine, dried over magnesium sulfate and concentrated, affording as residue 13.2 g of resinous dimethyl 3,5-cyclohexanedionecarboxamide which is obtained in crystalline form after purification by chromatography through a column of silica gel eluted with hexane/ether. Melting point 152°-155° C.

(b) The 13.2 g of dimethyl 3,5-cyclohexanedionecarboxamide obtained in (a) are dissolved in 100 ml of ethylene chloride together with 6.9 ml of pyridine. With stirring, 8.5 ml of butyryl chloride are added dropwise to this solution. The ensuing reaction is slightly exothermic. The resultant yellow suspension is stirred for 14 hours at room temperature, then washed with 1N hydrochloric acid and brine, dried over magnesium sulfate and concentrated. The residue is dissolved in 100 ml of dichloroethane and the solution is boiled at reflux for 2 hours with 0.5 g of 4-dimethylaminopyridine and 0.1 ml of butyryl chloride. After cooling, the reaction mixture is washed with 20 ml of 1 n hydrochloric acid saturated with NaCl, dried over magnesium sulfate and concentrated. The residue is purified by chromatography through a column of silica gel eluted with ethyl acetate, affording 7.8 g of dimethyl 4-butyryl-3,5-cyclohexanedionecarboxamide as a pale oil.

(c) A mixture of 4.3 g of dimethyl 4-butyryl-3,5-cyclohexanedionecarboxamide obtained in (b), 1.9 g of ethoxyamine hydrochloride, 1.4 g of potassium carbonate in 50 ml of chloroform and 5 ml of methanol is stirred for 24 hours at room temperature. The reaction mixture is then washed with 1N hydrochloric acid, dried over magnesium sulfate and concentrated.

The oily residue is then purified by chromatography through a column of silica gel eluted with ethyl acetate. The solvent is evaporated and the residual oil crystallises on standing. Yield: 2 g of title compound with a melting point of 54°-58° C.

The following 3,5-cyclohexanedione-1-carboxylic acid derivatives of formula II required as intermediates are prepared in a manner analogous to that of this Example.

TABLE 1

$$\text{(II)}$$

Structure: cyclohexane ring with A—C(=O)— at position 1, C(=O) at 3 and 5, and =NOR$_1$ with R substituent on the carbon adjacent to one ketone.

| Comp. | A | R | R$_1$ | Physical data |
|---|---|---|---|---|
| 1.001 | OCH$_3$ | C$_3$H$_7$n | C$_2$H$_5$ | n$_D^{27}$ 1.5100 |
| 1.002 | OC$_2$H$_5$ | C$_5$H$_7$ | C$_2$H$_5$ | n$_D^{27}$ 1.5002 |
| 1.003 | OC$_2$H$_5$ | C$_3$H$_7$n | CH$_2$CH=CH$_2$ | n$_D^{27}$ 1.5112 |
| 1.004 | OC$_4$H$_9$iso | C$_3$H$_7$n | C$_2$H$_5$ | n$_D^{27}$ 1.4929 |
| 1.005 | OC$_4$H$_9$iso | C$_3$H$_7$n | CH$_2$CH=CH$_2$ | n$_D^{27}$ 1.4989 |
| 1.006 | OCH$_2$SCH$_3$ | C$_3$H$_7$n | C$_2$H$_5$ | n$_D^{25}$ 1.5198 |
| 1.007 | OCH$_2$SCH$_3$ | C$_3$H$_7$n | CH—O=CH | |
| 1.008 | OC$_3$H$_7$iso | C$_3$H$_7$n | C$_2$H$_5$ | n$_D^{25}$ 1.5003 |
| 1.009 | OC$_3$H$_7$iso | C$_3$H$_7$n | CH$_2$—CH=CH$_2$ | n$_D^{25}$ 1.5088 |
| 1.010 | OC$_3$H$_7$iso | C$_3$H$_7$n | CH$_2$CCl=CH$_2$ | |
| 1.011 | OC$_2$H$_4$SCH$_3$ | C$_3$H$_7$n | C$_2$H$_5$ | |
| 1.012 | OC$_2$H$_4$SCH$_3$ | C$_3$H$_7$n | CH$_2$—CH=CH$_2$ | |
| 1.013 | OC$_2$H$_4$SCH$_3$ | C$_3$H$_7$n | C$_2$H$_4$Cl | |
| 1.014 | OC$_2$H$_4$OCH$_3$ | C$_3$H$_7$n | CH$_3$ | |
| 1.015 | OC$_2$H$_4$OCH$_3$ | C$_3$H$_7$n | C$_2$H$_5$ | |
| 1.016 | OC$_3$H$_6$Cl | C$_3$H$_7$n | C$_2$H$_5$ | |
| 1.017 | OCH$_2$—C$_6$H$_5$ (benzyloxymethyl) | C$_3$H$_7$n | C$_2$H$_5$ | |
| 1.018 | OCH$_2$—C$_6$H$_5$ (benzyloxymethyl) | C$_3$H$_7$n | CH$_2$—CH=CH$_2$ | |
| 1.019 | OCH$_2$—C$_6$H$_4$—OCH$_3$ (4-methoxybenzyloxymethyl) | C$_3$H$_7$n | C$_6$H$_{13}$n | |
| 1.020 | CH$_2$CH=CH$_2$ | C$_3$H$_7$n | C$_6$H$_{13}$n | |
| 1.021 | OCH$_2$—CH=CH$_2$ | C$_3$H$_7$n | CH$_3$ | |
| 1.022 | OC$_2$H$_4$Cl | C$_3$H$_7$n | CH$_2$—C=CH$_2$ | |
| 1.023 | OCH$_2$CCl=CH$_2$ | C$_3$H$_7$n | C$_2$H$_4$Cl | |
| 1.024 | OCH—C=CH | C$_3$H$_7$n | C$_6$H$_{13}$ | |
| 1.025 | OCH$_3$ | C$_6$H$_{13}$n | C$_2$H$_5$ | |
| 1.026 | OC$_2$H$_5$ | cyclopropyl | CH$_2$CH=CH$_2$ | |
| 1.027 | OCH$_3$ | cyclohexyl | C$_2$H$_5$ | |
| 1.028 | OC$_6$H$_{13}$n | CH$_3$ | C$_4$H$_9$n | |
| 1.029 | OCH$_2$SCH$_3$ | CH$_3$ | C$_4$H$_9$sec | |
| 1.030 | OC$_2$H$_5$ | CH$_2$SCH$_3$ | C$_2$H$_5$ | |
| 1.031 | OC$_2$H$_5$ | C$_2$H$_4$OCH$_3$ | CH$_2$—C=CH | |
| 1.032 | OC$_4$H$_9$tert | CHCl—CH$_3$ | C$_2$H$_5$ | |
| 1.033 | NH$_2$ | C$_3$H$_7$n | C$_2$H$_5$ | |
| 1.034 | NH$_2$ | C$_3$H$_7$n | CH$_2$—CH=CH$_2$ | m.p. 127–129° |
| 1.035 | NH$_2$ | C$_2$H$_5$ | C$_2$H$_5$ | |
| 1.036 | NH$_2$ | C$_2$H$_5$ | CH$_2$—CCl=CH$_2$ | |
| 1.037 | N(CH$_3$)$_2$ | C$_3$H$_7$n | C$_2$H$_5$ | m.p. 54–58° |
| 1.038 | N(CH$_3$)$_2$ | C$_3$H$_7$i | CH—CH=CH$_2$ | m.p. 59–65° |
| 1.039 | N(CH$_3$)$_2$ | C$_3$H$_7$i | CH$_3$ | |
| 1.040 | N(CH$_3$)$_2$ | C$_3$H$_7$i | C$_3$H$_6$Br | |
| 1.041 | NHC$_4$H$_9$iso | C$_3$H$_7$n | C$_2$H$_5$ | m.p. 88–90° |
| 1.042 | NHC$_4$H$_9$iso | C$_3$H$_7$n | CH$_3$ | |
| 1.043 | NHC$_4$H$_9$iso | C$_3$H$_7$n | CH$_2$CH=CH$_2$ | m.p. 100–102° |
| 1.044 | NHC$_4$H$_9$iso | CH$_3$ | CH$_2$C=CH | |
| 1.045 | N(CH$_2$—CH=CH$_2$)$_2$ | cyclopropyl | C$_2$H$_5$ | |
| 1.046 | NHCH$_2$—C=CH | CH$_2$OCH$_3$ | C$_5$H$_{11}$sec | |

TABLE 1-continued $$\text{(II)}$$

Structure (II): cyclohexane-1,3-dione with A-C(=O)- at position 5 and =NOR₁ oxime with R group at position 2.

| Comp. | A | R | R₁ | Physical data |
|---|---|---|---|---|
| 1.047 | NHCH₂-C₆H₅ (benzyl-NH) | C₃H₇n | C₂H₅ | m.p. 116-119° |
| 1.048 | NHCH₂-C₆H₄-NO₂ | C₂H₄Cl | C₂H₄F | |
| 1.049 | N(CH₃)CH₂-C₆H₅ | C₂H₄OC₂H₄ | CH₂CF₃ | |
| 1.050 | NHC₂H₄OCH₃ | C₃H₇n | C₂H₅ | |
| 1.051 | NHC₂H₄SCH₃ | C₄H₉iso | CH₃ | |
| 1.052 | piperidino | C₃H₇i | CH₂—CH=CH₂ | |
| 1.053 | morpholino | C₆H₁₃ | C₂H₅ | |
| 1.054 | N(CH₃)OCH₃ | C₃H₇n | C₂H₅ | $n_D^{25}$ 1.5122 |
| 1.055 | N(CH₃)OCH₃ | C₃H₇n | CH₂CH=CH₂ | |
| 1.056 | N(CH₃)OCH₃ | C₃H₇n | CH₂CH=CHCl | oil |
| 1.057 | N(C₂H₅)₂ | C₃H₇n | C₂H₅ | wax |
| 1.058 | N(C₂H₅)₂ | C₃H₇n | CH₂CH=CH₂ | |
| 1.059 | N(CH₃)₂ | cyclopropyl | C₂H₅ | |
| 1.060 | NH-C₆H₅ | cyclopropyl | CH₂CH=CH₂ | |
| 1.061 | N(CH₃)OCH₃ | C₂H₅ | C₂H₅ | |
| 1.062 | NHCH₂-C₆H₅ | C₄H₉iso | C₂H₅ | |
| 1.063 | NHCH₂-C₆H₅ | cyclopropyl | CH₂CH=CH₂ | |
| 1.064 | NH-C₆H₅ | C₃H₇n | C₂H₅ | m.p. 123-126° |
| 1.065 | NH-C₆H₅ | C₃H₇n | CH₂CH=CH₂ | wax |
| 1.066 | NH-C₆H₅ | CH₃ | CH₂CH=CH₂ | |

TABLE 1-continued $$\text{(II)}$$

Structure: cyclohexane-1,3-dione with A-C(=O)- at position 5 and =NOR$_1$ with R substituent at position 2.

| Comp. | A | R | R$_1$ | Physical data |
|---|---|---|---|---|
| 1.067 | 4-NH-phenyl | C$_6$H$_{13}$n | C$_2$H$_5$ | |
| 1.068 | 4-NH-phenyl-3-CF$_3$ | C$_3$H$_7$n | C$_2$H$_5$ | |
| 1.069 | 4-NH-phenyl-4-OCH$_3$ | C$_6$H$_{13}$n | C$_2$H$_5$ | |
| 1.070 | 4-NH-phenyl-4-Cl | C$_6$H$_{13}$n | CH$_2$CH=CH$_2$ | |
| 1.071 | N(CH$_3$)-phenyl | C$_6$H$_{13}$n | CH$_2$CH=CH$_2$ | |
| 1.072 | cyclopropylamino | C$_6$H$_{13}$n | C$_2$H$_5$ | |
| 1.073 | NHC$_6$H$_{13}$n | CH$_3$ | C$_2$H$_5$ | |
| 1.074 | NH-phenyl | C$_3$H$_7$n | CH$_2$CH=CHCl | |
| 1.075 | N(CH$_3$)$_2$ | C$_3$H$_7$n | CH$_2$CH=CHCl | |
| 1.076 | NHCH$_2$-phenyl | C$_3$H$_7$n | CH$_2$CH=CHCl | |
| 1.077 | NHC$_2$H$_4$SCH$_3$ | C$_3$H$_7$n | C$_2$H$_5$ | m.p. 61–67° |
| 1.078 | NHC$_2$H$_4$SCH$_3$ | C$_3$H$_7$n | CH$_2$CH=CH$_2$ | |
| 1.079 | NHC$_2$H$_4$SCH$_3$ | C$_3$H$_7$n | CH$_2$CH=CHCl | |
| 1.080 | N(CH$_3$)$_2$ | cyclopropyl | CH$_2$CH=CH$_2$ | |
| 1.081 | N(CH$_3$)$_2$ | C$_3$H$_7$n | C$_4$H$_9$n | m.p. 67–70° |
| 1.082 | N(CH$_3$)$_2$ | C$_3$H$_7$n | C$_6$H$_{13}$n | m.p. 65–68° |
| 1.083 | N(CH$_3$)$_2$ | C$_2$H$_5$ | C$_2$H$_5$ | oil |
| 1.084 | N(CH$_3$)$_2$ | C$_2$H$_5$ | CH$_2$CH=CH$_2$ | m.p. 82–83° |
| 1.085 | N(CH$_3$)$_2$ | C$_6$H$_{13}$N | C$_2$H$_5$ | |
| 1.086 | N(CH$_3$)$_2$ | C$_5$H$_{11}$n | CH$_2$CH=CH$_2$ | m.p. 64–66° |
| 1.087 | azetidinyl (N-ring) | C$_3$H$_7$n | C$_2$H$_5$ | m.p. 77–85° |
| 1.088 | azetidinyl (N-ring) | C$_8$H$_7$n | C$_2$H$_5$ | |

TABLE 1-continued $$\text{(II)}$$

Structure: cyclohexane-1,3-dione with A-C(=O)- substituent and =NOR₁ oxime with R group

| Comp. | A | R | R₁ | Physical data |
|-------|---|---|----|----|
| 1.089 | azetidinyl (N-ring) | C₃H₇n | CH₂CH=CHCl | |
| 1.090 | NHCH₃ | C₃H₇n | C₂H₅ | m.p. 138–140° |
| 1.091 | NHCH₃ | C₃H₇n | CH₂CH=CH₂ | |
| 1.092 | NHCH₃ | C₃H₇n | CH₃ | m.p. 139–141° |
| 1.093 | N(CH₃)-phenyl | C₃H₇n | CH₂CH=CHCl | m.p. 52–56° |
| 1.094 | N(CH₃)-phenyl | C₃H₇n | C₂H₅ | m.p. 93–95° |
| 1.095 | N(CH₂CH=CH₂)₂ | C₃H₇n | C₂H₅ | |
| 1.096 | N(CH₂CH=CH₂)₂ | C₃H₇n | CH₂CH=CH₂ | oil |
| 1.097 | N(CH₂CH=CH₂)₂ | C₃H₇n | CH₂CH=CHCl | oil |
| 1.098 | N(CH₂CH=CH₂)₂ | C₃H₇n | CH₃ | |
| 1.099 | NHCH₃ | C₃H₇n | C₆H₁₃n | |
| 1.100 | NHCH₃ | C₃H₇n | C₄H₉n | |
| 1.101 | NHCH₃ | C₅H₁₁n | CH₂CH=CH₂ | |
| 1.102 | NHCH₃ | C₆H₁₃n | C₄H₉n | |
| 1.103 | NHC₂H₄SCH₃ | C₂H₅ | CH₂CH=CH₂ | |
| 1.104 | NHC₂H₄SC₃H₇i | C₃H₇n | CH₂CH=CH₂ | |
| 1.105 | NHC₂H₄SC₃H₇i | C₃H₇n | C₄H₉n | |
| 1.106 | N(CH₃)C₂H₅ | C₃H₇n | CH₂CH=CH₂ | |
| 1.107 | N(CH₃)C₂H₅ | C₃H₇n | C₄H₉n | |
| 1.108 | N(CH₃)C₂H₅ | C₃H₇n | CH₂CH=CHCl | |
| 1.109 | N(CH₃)₂ | C₅H₁₁n | C₂H₅ | |
| 1.110 | OCH₃ | CH₃ | C₂H₅ | $n_n^{30}$ 1.5077 |
| 1.111 | N(CH₃)₂ | C₃H₇n | CH₂CH=CHCl | oil |
| 1.112 | OC₂H₅ | C₃H₇n | C₄H₉n | oil |
| 1.113 | N(CH₃)₂ | C₂H₅ | C₄H₉n | m.p. 59–63° |
| 1.114 | N(CH₃)-phenyl | C₃H₇n | C₄H₉i | oil |
| 1.115 | N(CH₃)₂ | C₃H₇n | C₄H₉i | oil |
| 1.116 | OH | C₃H₇n | C₄H₉n | oil |
| 1.117 | N(CH₃)₂ | C₂H₅ | CH₂CH=CHCl | m.p. 69–73° |
| 1.118 | N(C₂H₅)₂ | C₂H₅ | C₂H₅ | m.p. 90–93° |
| 1.119 | N(C₂H₅)₂ | C₂H₅ | CH₂CH=CH₂ | m.p. 73–76° |
| 1.120 | azetidinyl (N-ring) | C₂H₅ | C₂H₅ | m.p. 58–60° |
| 1.121 | azetidinyl (N-ring) | C₂H₅ | CH₂CH=CH₂ | m.p. 70–72° |
| 1.122 | N(CH₃)₂ | C₃H₇n | CH₂C(CH₃)=CH₂ | m.p. 55–57° |

TABLE 1-continued (II)

| Comp. | A | R | R₁ | Physical data |
|---|---|---|---|---|
| 1.123 | N(CH₃)₂ | CH₃ | CH₂CH=CHCl | wax |

EXAMPLE 2

Preparation of dimethyl 3-acetoxy-4-(1-ethoximinobutyl)-5-oxocyclohex-3-enecarboxamide

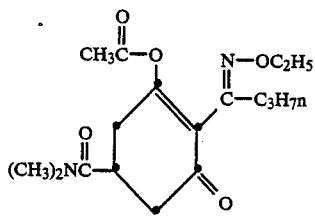

With stirring, 8.5 ml of a 2M aqueous solution of NaOH are added dropwise to a solution of 5 g of dimethyl 4-(1-ethoxyaminobutylidene)-3,5-cyclohexanedionecarboxamide in 70 ml of acetone. After 20 minutes the solution is concentrated by rotary evaporation to dryness. The residue is suspended in 70 ml of acetone and, after the addition of 1.22 ml of acetyl chloride, stirred for 2 hours at room temperature. The reaction solution is concentrated in vacuo, the residue is taken up in acetyl acetate, the solution is washed with NaOH solution and a saturated solution of NaCl, dried and concentrated, affording 2.3 g of the title compound as an oil.

EXAMPLE 3

Preparation of dimethyl 3-benzoyloxy-4-(1-ethoximinobutyl)-5-oxocyclohex-3-enecarboxamide

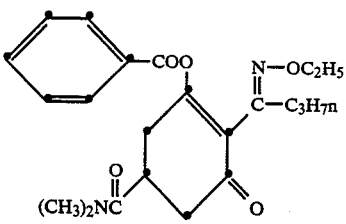

1.8 g of potassium carbonate are added to a solution of 3.9 g of dimethyl 4-(1-ethoximinobutylidene)-3,5-cyclohexanedionecarboxamide and 1.55 ml of benzoyl chloride in 80 ml of acetone and the reaction mixture is stirred for 15 hours at room temperature. The solution is then diluted with 80 ml of acetyl acetate, filtered and concentrated by rotary evaporation at 45° C. in vacuo, affording as residue 4.6 g of the title compound in the form of an oil.

EXAMPLE 4

Preparation of dimethyl 4-(1-ethoximinobutyl)-3-methoxy-5-oxocyclohex-3-enecarboxamide

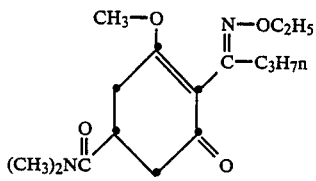

2.4 g of potassium carbonate are added to a solution of 5 g of dimethyl 4-(1-ethoxyaminobutylidene)-3,5-cyclohexanedionecarboxamide and 0.85 ml of dimethylsulfate in 70 ml of acetone and the reaction mixture is stirred for 15 hours at room temperature. The reaction mixture is then diluted with 70 ml of chloroform, filtered and concentrated by rotary evaporation. The residual oil is separated by chromatography through a column of silica gel into its isomers, affording 1.6 g of an isomer (trans-isomer) with a melting point of 188°–194° C. and 0.5 g of a second isomer (cis-isomer) with a melting point of 147°–150° C.

The preparation of the starting material is described in Example 1a–1c.

Starting from compounds of Table 1, the following compounds of Table 2 are prepared by procedures similar to those described in Examples 2 to 4.

TABLE 2

| Comp. | A | R | R₁ | B |
|---|---|---|---|---|
| 2.01 | —OCH₃ | C₃H₇(n) | —C₂H₅ | CH₃ |
| 2.02 | —OCH₃ | C₃H₇(n) | —C₂H₅ | COCH₃ |
| 2.03 | —OCH₃ | C₃H₇(n) | —C₂H₅ | benzoyl |
| 2.04 | —OCH₃ | C₃H₇(n) | —C₂H₅ | benzyl |
| 2.05 | —OCH₃ | C₃H₇(n) | —C₂H₅ | p-tolylsulfonyl |
| 2.06 | —OCH₃ | C₃H₇(n) | —CH₂CH=CH₂ | —COCH₃ |
| 2.07 | —OCH₃ | C₃H₇(n) | —CH₂CH=CH₂ | —SO₂CH₃ |
| 2.08 | —OCH₃ | C₃H₇(n) | —CH₂CH=CH₂ | —C₂H₅ |
| 2.09 | OC₃H₇(i) | C₃H₇(n) | —C₂H₅ | —COCH₂ |

TABLE 2-continued

| Comp. | A | R | R₁ | B | |
|---|---|---|---|---|---|
| 2.10 | OC$_3$H$_7$(i) | C$_3$H$_7$(n) | —C$_2$H$_5$ | benzoyl | |
| 2.11 | OC$_3$H$_7$(i) | C$_3$H$_7$(n) | —CH$_2$CH=CH$_2$ | 3-chlorobenzoyl | |
| 2.12 | OC$_3$H$_7$(i) | C$_3$H$_7$(n) | —CH$_2$CH=CH$_2$ | phenylsulfonyl | |
| 2.13 | OC$_3$H$_7$(i) | C$_3$H$_7$(n) | —CH$_2$CH=CH$_2$ | —CH$_2$—CH=CH$_2$ | |
| 2.14 | N(CH$_3$)$_2$ | C$_3$H$_7$(n) | —C$_2$H$_5$ | —COCH$_3$ | Example 2 |
| 2.15 | N(CH$_3$)$_2$ | C$_3$H$_7$(n) | —C$_2$H$_5$ | benzoyl | Example 3 |
| 2.16 | N(CH$_3$)$_2$ | C$_3$H$_7$(n) | —C$_2$H$_5$ | —CH$_3$ | Example 4 |
| 2.17 | N(CH$_3$)$_2$ | C$_3$H$_7$(n) | —C$_2$H$_5$ | p-tolylsulfonyl | |
| 2.18 | N(CH$_3$)$_2$ | C$_3$H$_7$(n) | —CH$_2$CH=CH$_2$ | —COCH$_3$ | |
| 2.19 | N(CH$_3$)$_2$ | C$_3$H$_7$(n) | —CH$_2$CH=CH$_2$ | benzoyl | |
| 2.20 | N(CH$_3$)$_2$ | C$_3$H$_7$(n) | —CH$_2$CH=CH$_2$ | —CH$_3$ | |
| 2.21 | N(CH$_3$)$_2$ | C$_3$H$_7$(n) | —CH$_2$CH=CH$_2$ | p-tolylsulfonyl | |
| 2.22 | N(CH$_3$)$_2$ | C$_3$H$_7$(n) | —CH$_2$CH=CHCl | n-butyryl | |
| 2.23 | N(CH$_3$)$_2$ | C$_3$H$_7$(n) | —CH$_2$CH=CHCl | p-chlorobenzoyl | |
| 2.24 | N(CH$_3$)$_2$ | C$_2$H$_5$ | —CH$_2$CH=CHCl | —COCH$_3$ | |
| 2.25 | N(CH$_3$)$_2$ | C$_2$H$_5$ | —CH$_2$CH=CHCl | n-butyryl | |
| 2.26 | N(CH$_3$)$_2$ | C$_2$H$_5$ | —CH$_2$CH=CHCl | —CH$_2$—C≡CH | |
| 2.27 | N(CH$_3$)$_2$ | C$_6$H$_{13}$ | —CH$_3$ | —CH$_3$ | |
| 2.28 | N(CH$_3$)$_2$ | C$_6$H$_{13}$ | —C$_2$H$_5$ | —COCH=CH$_2$ | |
| 2.29 | NH$_2$ | C$_3$H$_7$(n) | —CH$_2$CH=CH$_2$ | —COCH$_3$ | |
| 2.30 | NH$_2$ | C$_3$H$_7$(n) | —CH$_2$CH=CH$_2$ | —COCH$_2$CH$_3$ | |
| 2.31 | NH$_2$ | C$_3$H$_7$(n) | —CH$_2$CH=CH$_2$ | benzoyl | resin |
| 2.32 | NH$_2$ | C$_3$H$_7$(n) | —CH$_2$CH=CH$_2$ | p-tolylsulfonyl | |
| 2.33 | NH$_2$ | C$_3$H$_7$(n) | —CH$_2$CH=CH$_2$ | —CH$_3$ | |
| 2.34 | NH$_2$ | C$_3$H$_7$(n) | —CH$_2$CH=CH$_2$ | benzyl | |
| 2.35 | NH$_2$ | C$_3$H$_7$(n) | C$_2$H$_5$ | —COCH$_3$ | |
| 2.36 | NH$_2$ | C$_3$H$_7$(n) | —C$_2$H$_5$ | —SO$_2$CH$_3$ | |
| 2.37 | NH$_2$ | C$_3$H$_7$(n) | —C$_2$H$_5$ | p-anisoyl | |
| 2.38 | NH$_2$ | C$_3$H$_7$(n) | —C$_2$H$_5$ | —CH$_2$—CH$_3$ | |
| 2.39 | NHCH$_3$ | C$_3$H$_7$(n) | —CH$_2$CH=CH$_2$ | —COCH$_3$ | |
| 2.40 | NHCH$_3$ | C$_3$H$_7$(n) | —CH$_2$CH=CH$_2$ | benzoyl | |
| 2.41 | NHCH$_3$ | C$_3$H$_7$(n) | —CH$_2$CH=CH$_2$ | benzyl | |
| 2.42 | NHCH$_3$ | C$_3$H$_7$(n) | —C$_2$H$_5$ | —CH$_3$ | |
| 2.43 | NHCH$_3$ | C$_3$H$_7$(n) | —C$_2$H$_5$ | benzoyl | |
| 2.44 | NHCH$_3$ | C$_3$H$_7$(n) | —C$_2$H$_5$ | —SO$_2$CH$_3$ | |
| 2.45 | NHCH$_3$ | C$_3$H$_7$(n) | —C$_4$H$_9$(n) | benzoyl | |
| 2.46 | NHCH$_3$ | C$_3$H$_7$(n) | —C$_4$H$_9$(n) | —CH$_3$ | |
| 2.47 | anilino | C$_3$H$_7$(n) | —C$_2$N$_5$ | —CH$_3$ | |
| 2.48 | anilino | C$_3$H$_7$(n) | —C$_2$N$_5$ | —COCH$_3$ | |
| 2.49 | anilino | C$_3$H$_7$(n) | —C$_2$N$_5$ | benzoyl | |
| 2.50 | anilino | C$_3$H$_7$(n) | —CH$_2$CH=CH$_2$ | benzyl | |
| 2.51 | anilino | C$_3$H$_7$(n) | —CH$_2$CH=CH$_2$ | p-tolylsulfonyl | |
| 2.52 | benzyl-amino | C$_3$H$_7$(n) | —CH$_2$CH=CH$_2$ | —COCH$_3$ | |
| 2.53 | benzyl-amino | C$_3$H$_7$(n) | —CH$_2$CH=CH$_2$ | —CH$_3$ | |
| 2.54 | benzyl-amino | C$_3$H$_7$(n) | —C$_2$H$_5$ | —CH$_3$ | |
| 2.55 | benzyl-amino | C$_3$H$_7$(n) | —C$_2$H$_5$ | —CH$_2$CH=CH$_2$ | |
| 2.56 | benzyl-amino | C$_3$H$_7$(n) | —C$_2$H$_5$ | m-anisoyl | |
| 2.57 | benzyl-amino | C$_3$H$_7$(n) | —C$_2$H$_5$ | phenylsulfonyl | |
| 2.58 | N(CH$_3$)$_2$ | C$_3$H$_7$(n) | —C$_4$H$_9$(n) | benzoyl | oil |
| 2.59 | N(CH$_3$)$_2$ | C$_3$H$_7$(n) | —C$_2$H$_5$ | p-anisoyl | m.p. 105–108° |
| 2.60 | N(CH$_3$)$_2$ | C$_3$H$_7$(n) | —C$_2$H$_5$ | benzyl | m.p. 135–139° |
| 2.61 | N(CH$_3$)$_2$ | C$_3$H$_7$(n) | —C$_2$H$_5$ | —CH$_2$—CH=CH$_2$ | m.p. 96–103° |

FORMULATION EXAMPLES

EXAMPLE 5

Formulation Examples for compounds of formula I (percentages are by weight)

| (a) Wettable powders | (a) | (b) | (c) |
|---|---|---|---|
| compound of formula I | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| compound of formula I | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| compound of formula I | 3% |
| polyethylene glycol (mol. wt. 200) | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| compound of formula I | 5% |
| isopropylamine | 1% |
| octylphenol polyethylene glycol ether (78 moles of ethylene oxide) | 3% |
| water | 91% |

BIOLOGICAL EXAMPLES

EXAMPLE 6

Preemergence herbicidal action

In a greenhouse, plant seeds are sown in flower pots of 11 cm diameter. Immediately after sowing, the surface of the soil is treated with an aqueous emulsion of test compound at a concentration of 4 kg a.i./ha. The pots are then kept in the greenhouse at 22°–25° C. and 50–70% relative humidity. 3 weeks later the test is evaluated and the action on the test plants is assessed. The compounds of Table 1 exhibit good activity, especially against the monocot test plants.

EXAMPLE 7

Postemergence herbicidal action

Various cultivated plants and weeds are grown from seeds in pots in a greenhouse until they have attained the 4- to 6-leaf stage. The plants are then sprayed with an aqueous emulsion of test compound (obtained from a 25% emulsifiable concentrate) at a concentration of 4 kg/ha. The treated plants are then kept under optimum conditions of light, regular watering, temperature (22°–25° C.) and relative humidity (50–70%). The test is evaluated 15 days after treatment. Compounds of Table 1 exhibit good herbicidal activity, especially against the monocot test plants.

EXAMPLE 8

Growth inhibition of tropical leguminous cover crops

The test plants (*Centrosema plumieri* and *Centrosema pubescens*) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

EXAMPLE 9

Growth regulation of soybeans

Soybeans of the "Hark" variety are sown in plastic containers in an earth/peat/sand mixture (6:3:1). The containers are put into a climatic chamber and the plants develop to the 5–6 trefoil leaf stage after about 5 weeks by optimum control of temperature, light, fertiliser addition, and watering. The plants are then sprayed with an aqueous mixture of a compound of formula I until thoroughly wetted. The concentration corresponds to up to 100 g a.i. per hectare. Evaluation is made about 5 weeks after application. Compared with untreated controls, the compounds of formula I markedly increase the number and weight of the harvested siliquae on the leading shoot.

EXAMPLE 10

Growth inhibition of cereals

Summer barley (*Hordeum vulgare*) and summer rye (*Secale*) are sown in sterilised soil in plastic beakers in a greenhouse and watered as required. The cereal shoots are treated about 21 days after sowing with an aqueous spray mixture of a compound of Table 1. The concentration corresponds to up to 100 g of active ingredient per hectare. Evaluation of the growth of the cereals is made 21 days after application. A comparison with untreated controls shows that the growth of treated cereal plants is reduced (60–90% of the controls) and that the diameter of the stalks has in some cases increased.

EXAMPLE 11

Growth inhibition of grasses

Seeds of the grasses *Lolium perenne, Poa pratensis, Festuca ovina, Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of Table 1. The concentration of test compound corresponds to a rate of application of up to 100 g a.i. per hectare. The growth of the grasses is evaluated 21 days after application. The test compounds effect a reduction in new growth in the range of 10–30% in comparison with untreated controls.

What is claimed is:

1. A cyclohexenone carboxylic acid derivative of formula I

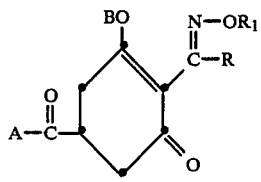

wherein
A is $-NR_3R_4$
B is $-R_6$
R is $C_1-C_6$alkyl or $C_3-C_6$cycloalkyl, each unsubstituted or substituted by halogen, $C_1-C_4$alkoxy or $C_1-C_4$alkylthio,
$R_1$ is $C_1-C_6$alkyl, $C_1-C_6$haloalkyl, $C_3-C_6$alkenyl, $C_3-C_6$haloalkenyl or $C_3-C_6$alkynyl,
$R_3$ is hydrogen, $C_1-C_6$alkyl, $C_1-C_6$haloalkyl, $C_2-C_{10}$alkoxyalkyl, $C_2-C_{10}$alkylthioalkyl; or is $C_3-C_6$alkenyl which is unsubstituted or substituted by halogen, $C_1-C_4$alkyl, $C_1-C_4$alkoxy or $C_1-C_4$alkylthio; or is $C_3-C_6$alkynyl; or is phenyl or benzyl, the phenyl nucleus of which is unsubstituted or substituted by halogen, $C_1-C_4$alkyl, $C_1-C_4$alkoxy, $C_1-C_4$haloalkoxy, nitro or cyano,
$R_4$ is $C_1-C_4$alkoxy or has the same meaning as $R_3$, or $R_3$ and $R_4$ together with the nitrogen atom to which they are attached are also a saturated 5- or 6-membered heterocycle and
$R_6$ is $C_1-C_6$alkyl, $C_3-C_6$alkenyl, $C_3-C_6$alkynyl; or is benzyl, the nucleus of which unsubstituted or substituted by halogen, $C_1-C_4$alkyl, $C_1-C_4$alkoxy, $C_1-C_4$haloalkoxy, nitro or cyano.

2. Dimethyl-4-(1-ethoximinobutyl)-3-benzyloxy-5-oxocyclohex-3-ene-carboxamide according to claim 1.

3. Dimethyl-4-(1-ethoximinobutyl)-3-allyloxy-5-oxocyclohex-3-ene-carboxamide according to claim 1.

4. Dimethyl 4-(1-ethoximinobutyl)-3-methoxy-5-oxocyclohex-3-enecarboxamide according to claim 1.

5. A herbicidal and plant growth regulating composition which comprises, an effective amount of a cyclohexenonecarboxylic acid derivative according to claim 1, together with carrier and/or other adjuvants.

6. A method of inhibiting the growth of grasses in a lawn, which comprises applying to the lawn an effective amount of a cyclohexenonecarboxylic acid derivative according to claim 1.

7. A method of selectively controlling weeds pre- or postemergence in crops of useful plants, which comprises treating said useful plants or the crop area thereof with an effective amount of a cyclohexenonecarboxylic acid derivative according to claim 1.

8. A method of regulating plant growth, which comprises treating said plants, parts of plants or seeds of said plants with an effective amount of a cyclohexenonecarboxylate according to claim 1.

* * * * *